United States Patent [19]

Doria et al.

[11] 4,148,900

[45] Apr. 10, 1979

[54] 5:6-BENZO-γ-PYRONE DERIVATIVES AND PROCESS FOR THEIR PREPARATION

[75] Inventors: Gianfederico Doria; Piernicola Giraldi; Francesco Lauria; Maria L. Corno, all of Milan; Piero Sberze, Varese; Marcello Tibolla, Milan, all of Italy

[73] Assignee: Carlo Erba S.p.A., Milan, Italy

[21] Appl. No.: 833,962

[22] Filed: Sep. 16, 1977

Related U.S. Application Data

[60] Division of Ser. No. 691,488, Jun. 1, 1976, Pat. No. 4,115,567, which is a division of Ser. No. 660,383, Feb. 23, 1976, Pat. No. 4,065,467, which is a continuation of Ser. No. 536,476, Dec. 26, 1974, abandoned.

[30] Foreign Application Priority Data

Dec. 27, 1973 [IT] Italy .............. 32089 A/73
Jul. 4, 1974 [IT] Italy .............. 24777 A/74
Jul. 17, 1974 [IT] Italy .............. 25244 A/74

[51] Int. Cl.$^2$ .............. C07D 405/04; C07D 405/06
[52] U.S. Cl. .............. 424/263; 260/345.2; 260/308 D; 260/326.85; 260/326.87; 260/327 A; 260/327 C; 260/332.2 A; 260/340.3; 424/250; 424/269; 424/276; 544/111; 544/120; 544/124; 544/151; 548/336; 548/335; 542/441; 542/459; 542/430; 542/432; 542/454; 424/273 R; 544/230; 544/336; 544/376; 546/15; 546/269; 546/318

[58] Field of Search .............. 542/441; 260/295 F; 424/263

[56] References Cited

U.S. PATENT DOCUMENTS

| | | | |
|---|---|---|---|
| 3,522,245 | 7/1970 | Brinkhoff | 542/441 |
| 3,576,801 | 4/1971 | Brinkhoff | 542/454 |
| 3,600,403 | 8/1971 | Brinkhoff | 542/441 |
| 3,786,071 | 1/1974 | Cairns et al. | 260/345.2 |
| 3,816,466 | 6/1974 | Strandtmann | 260/345.2 |
| 3,825,574 | 7/1974 | Brown | 260/345.2 |
| 3,882,148 | 5/1975 | Augstein | 260/345.2 |

FOREIGN PATENT DOCUMENTS

781467 3/1968 Canada .............. 542/441

OTHER PUBLICATIONS

Shah et al., J. Am. Chem. Soc. 77(1955) p. 2223.
Shah et al., J. Chem. Soc. 1961 pp. 2663–2666.
Hsu et al., Chem. Abst. 54(1960) col. 4553g.
Koo, J. Org. Chem. 26(1961) pp. 2440–2444.
Owada, Chem. Abst. 78(1973) #84197.
Contessa et al., Chem. Abst. 72(1970) #98774.

Primary Examiner—Arthur P. Demers
Attorney, Agent, or Firm—Murray & Whisenhunt

[57] ABSTRACT

Chromone compounds carrying a pyridyl substituent at the 2-position are disclosed, such as, for instance, 6-carboxy-2-(2'-pyridyl)-chromone. The disclosed compounds are useful in the treatment of allergies.

20 Claims, No Drawings

5:6-BENZO-γ-PYRONE DERIVATIVES AND PROCESS FOR THEIR PREPARATION

This is a division of application Ser. No. 691,488 filed June 1, 1976 now U.S. Pat. No. 4,115,567 which is a divisional of Ser. No. 660,383, filed Feb. 23, 1976 now U.S. Pat. No. 4,065,467, which is a continuation of Ser. No. 536,476, filed Dec. 26, 1974, now abandoned.

This invention relates to a 5:6-benzo-γ-pyrone derivatives, to a process for their preparation and to pharmaceutical compositions containing them.

In particular, an object of the present invention is represented by new 5:6-benzo-γ-pyrone derivatives having the following general formula (I)

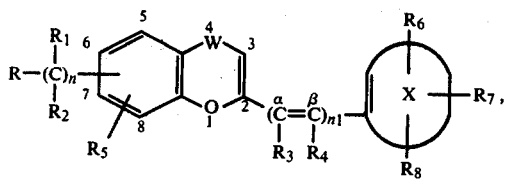

wherein:
n is zero or 1;
$n_1$ is zero or 1;
R may be:
(a) cyano, carboxy or the

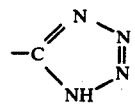

radical;
(b) —$COR_9$ may be —NHOH or a

radical wherein, each of $R_{10}$ and $R_{11}$ may hydrogen or $C_1$-$C_6$ alkyl, or, when $R_{10}$ is hydrogen, $R_{11}$ may also be the radical

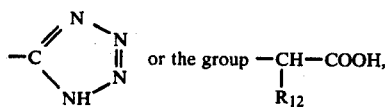

wherein $R_{12}$ is hydrogen or $C_1$-$C_6$ alkyl or $R_{10}$ and $R_{11}$, taken together with the nitrogen atom, may be a N-pyrrolinyl, piperidino or morpholino radical;

(c) $COOR_{13}$ wherein $R_{13}$ is a $C_1$-$C_{12}$ alkyl or alkenyl group, which may be unsubstituted or substituted by one or more substituents selected from the group consisting of halogen, carboxy, hydroxy, substituted or unsubstituted phenyl,

wherein $R_{10}$ and $R_{11}$ are as hereinabove defined, —$OR_{14}$ and —$OCOR_{14}$, wherein $R_{14}$ may be $C_1$-$C_6$ alkyl or one of the radicals:

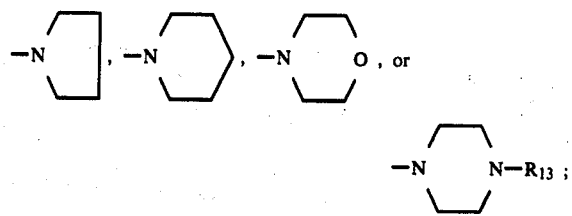

wherein $R_{13}$ is as hereabove defined;
each of $R_1$ and $R_2$, being the same or different, may be hydrogen or methyl;
Each of $R_3$ and $R_4$, being the same or different, mmay be hydrogen or $C_1$-$C_6$ alkyl;
each of $R_5$, $R_6$, $R_7$ and $R_8$, being the same or different, may be:
(a') hydrogen, halogen, hydroxy, nitro,

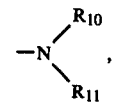

wherein $R_{10}$ and $R_{11}$ are as defined above;
(b') a radical —$(O)_m$—, wherein m is zero or 1, and $R_{13}$ is as hereabove defined;
(c') a radical —O—CO—$R_{15}$, wherein $R_{15}$ may have the same meanings above-mentioned for $R_{13}$ $R_{15}$ may be a group

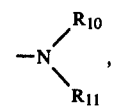

wherein $R_{10}$ and $R_{11}$ are as hereabove defined;
(d') a radical —S—$R_{13}$, wherein $R_{13}$ is as hereabove defined;
or $R_7$ and $R_8$, when placed on adjacent carbon atoms, may represent, taken together, a methylenedioxy, ethylenedioxy or propylenedioxy group;

X is phenyl or a pentatomic or hexatomic heteromonocyclic radical containing at least one double bond and one or two heteroatoms selected from the group consiting of nitrogen, sulphur and oxygen;

and wherein, when X is a nitrogen containing radical, a nitrogen atom may be bound to an oxygen atom to give the N-oxide; W may be

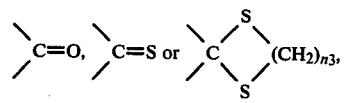

wherein $n_3$ is 2 or 3; and wherein the radical

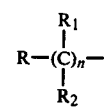

may be in the 6- or 7- position of the benzopyrone ring;
provided, however, that when W is —CO—, X is phenyl, R is 6-carboxy, $R_5$, $R_6$ and $R_7$ are hydrogen and $R_8$ is hydrogen or 3'-or 4'-hydroxy, methoxy or halogen, then at least one of n and $n_1$ is 1;

provided, furthermore, that when W is —CO—, X is phenyl, R is 6-carboxy, $R_5$ is 7-hydroxy and $R_6$, $R_7$ and $R_8$ are hydrogen then at least one of n and $n_1$ is 1;

provided, furthermore that when W is —CO—, X is phenyl, R is 6-carboxy, $R_5$ and $R_8$ are hydrogen, $R_7$ and $R_6$ togeter are 3', 4'-methylenedioxy, then at least one of n and $n_1$ is 1; provided, furthermore, that when W is —CO—, X is phenyl, R is 6-carboxy, $R_5$ is 5-ethoxy, $R_6$ is 4'-methoxy, and $R_7$ and $R_8$ are hydrogen, then at least one of n and $n_1$ is 1;

provided, furthermore, that when W is —CO—, X is phenyl, R is 7-carboxy, and $R_5$, $R_6$, $R_7$ and $R_8$ are hydrogen, that at least one of n and $n_1$ is 1;

and provided, furthermore, that when W is —CO—, X is phenyl, R is 6-carboxy, $R_1$ and $R_2$ are hydrogen, $R_5$ is 7-methoxy, $R_6$ is 4'-methoxy, $R_7$ and $R_8$ are hydrogen, and $n_1$ is zero, then n is zero.

Also the pharmaceutically acceptable salts of the compounds of formula (I) are included in the scope of the present invention. It is furthermore to be noted that in the compounds of the invention there are comprised also all the possible stereoisomers as well as their mixtures. In the compounds of the invention, (a) when X is phenyl, the numeration used is the following:

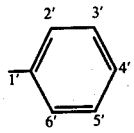

(b) when X is a pentatomic heteromonocyclic radical, the numeration used is the following:

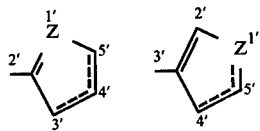

wherein Z is the heteroatom from which the numeration conventionally starts; ======= may be a simple or a double bond;

(c) when X is a hexatomic heteromonocyclic radical, the numeration used is the followng:

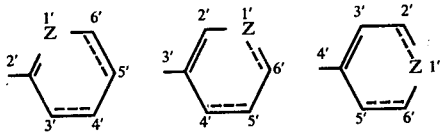

wherein Z and the symbol ======= are as hereinabove defined.

In the compounds of the invention, the alkyl, alkenyl, and alkoxy groups may be branched or straight chain.

When X is a heteromonocyclic radical, it is preferably furyl, thienyl, pyridyl, pyrazinyl, imidazolyl. Preferably, when $R_{13}$ is an alkyl group substituted by a phenyl, this phenyl may be in turn substituted by one or more substituents selected from the group consisting of hydroxy, alkyl, alkoxy, alkenyl, acetyl.

Particularly preferred new compounds of the invention are those of general formula (I) wherein:
n is zero;
$n_1$ is zero or 1;

R is a carboxy group or group —CONHCH$_2$COOH or a group —COOR$_{13}$, wherein
$R_{13}$ is selected from the group consisting of $C_1$—$C_6$ alkyl,

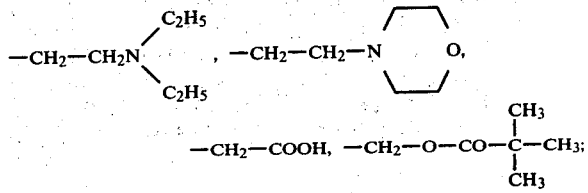

$R_3$ is hydrogen or methyl;
$R_4$ is hydrogen;
$R_5$ is hydrogen, allyl or propyl; $R_6$ is hydrogen; each of $R_7$ and $R_8$, being the same or different, may be
(a) hydrogen,
(b) a radical

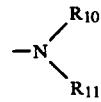

wherein each of $R_{10}$ and $R_{11}$ may be hydrogen or $C_1$-$C_6$ alkyl,
(c) a radical —(O)$_m$—$R_{13}$, wherein m may be zero or 1, and $R_{13}$ is a $C_1$-$C_6$ alkyl group, which may be unsubstituted or substituted with the hydroxy or a $C_1$-$C_6$ alkoxy group;

X is phenyl or a furyl or a pyridyl or pyrazinyl radical;

W is

and a pharmaceutically acceptable salt thereof;

provided, however, that when W is —CO—, X is phenyl, R is 6-carboxy, $R_5$, $R_6$ and $R_7$ are hydrogen and $R_8$ is hydrogen or 3'- or 4'-methoxy, then at least one of n and $n_1$ is 1.

Preferably, in the compounds of formula (I), when $R_5$ is propyl or allyl, the propyl or allyl group is in the 8-position. Preferably, when X is phenyl, $n_1$ is zero and $R_6$ and $R_7$ are hydrogen, $R_8$ is different from hydrogen and is preferably in the 2'-position of phenyl. When m is zero, $R_{13}$ is preferably a $C_1$-$C_3$ alkyl group; when m is 1, $R_{13}$ is preferably a $C_2$-$C_5$ alkyl group, in particular a propyl, isopropyl, butyl, 1-methyl-propyl, and 2-methyl-propyl group.

When $R_{13}$ is a substituted alkyl group, the substituent is preferably a hydroxy or ethoxy group.

Examples of pharmaceutically acceptable salts are sodium salts and the salts with 2-amino-ethanol and 2-amino-2-hydroxymethyl-1,3-propanediol.

The compounds excluded from general formula (I) as above reported, are already known in literature; however no reference exists either to a possible therapeutical use or to a possible pharmaceutical formulation containing said compounds. Another object of the present invention is represented by pharmaceutical compositions comprising a suitable carrier and/or diluent, and, as, an active principle, a compound of formula (I)

wherein n, $n_1$, R, $R_1$, $R_2$, $R_3$, $R_4$, $R_5$, $R_6$, $R_7$, $R_8$, X and W are as defined above, without any of the above-mentioned exclusions.

Examples of preferred compounds object of this invention, and respectively of preferred active substances of the pharmaceutical compositions of the invention are the following:

6-carboxy-2'-isopropoxy-flavone
6-carboxy-2'-propoxy-flavone
6-carboxy-2'-butoxy-flavone
6-carboxy-2'-(2-methyl-propoxy)-flavone
6-carboxy-2'-(1-methyl-propoxy)-flavone
6-carboxy-2'-(2-ethoxy-ethoxy)-flavone
6-carboxy-4'-(2-ethoxy-ethoxy)-flavone  6-carboxy-2'-(2-hydroxy-propoxy)-flavone
6-carboxy-2'-(3-hydroxy-propoxyl)flavone
6-carboxy-2'-(2,3-dihydroxy-propoxy)-flavone
6-carboxy-2'-(2-hydroxy-butoxy)-flavone
6-carboxy-2'-(2-hydroxy-2-methyl-propoxy)-flavone
6-carboxy-2'-(2-hydroxy-2-methyl-butoxy)-flavone
6-carboxy-2'-(2-hydroxy-3-methyl-butoxy)-flavone
6-carboxy-4'-(2-hydroxy-propoxy)-flavone
7-carboxy-2'-isopropoxy-flavone
7-carboxy-2'-(2-methyl-propoxy)-flavone
7-carboxy-2'-(1-methyl-propoxy)-flavone
7-carboxy-2'-(2-hydroxy-propoxy)-flavone
6-carboxy-2'-amino-flavone
6-carboxy-2'-dimethylamino-flavone
6-carboxy-2'-(N-methyl-N-isopropylamino)-flavone
6-carboxy-2'-isopropylamino-flavone
6-carboxy-2-(2'-pyridyl)-chromone
6-carboxy-2-(3'-pyridyl)-chromone
6-carboxy-2-(2'-pyridyl-N-oxide)-chromone
6-carboxy-2-(3'pyridyl-N-oxide)-chromone
6-carboxy-2-(2'-furyl)-chromone
6-carboxy-2-(2-imidazolyl)-chromone
6-carboxy-2-(5'-imidazolyl)-chromone
6-carboxy-2-(2'-pyrazinyl)-chromone
6-carboxy-2-(4'-isopropoxy-3'-pyridyl)-chromone
6-carboxy-2-[4'-(2-methyl-propoxy)-3'-pyridyl]-chromone
6-carboxy-2-[4'-(1-methyl-propoxy)-3'-pyridyl]-chromone
6-carboxy-2-[4'-(3-methyl-butoxy)-3'-pyridyl]-chromone
6-carboxy-2-(3'-isopropoxy-2'-pyridyl)-chromone
6-carboxy-2-[3'-(2-methyl-propoxy)-2'-pyridyl]-chromone
6-carboxy-2-[3'-(1-methyl-propoxy)-2'-pyridyl]-chromone
6-carboxy-2-[3'-(3-methyl-butoxy)-2'-pyridyl]-chromone
6-carboxy-2-[3'-(2-hydroxy-propoxy)-2'-pyridyl]-chromone
6-carboxy-8-allyl-2-(2'-pyrazinyl)-chromone
6-carboxy-8-allyl-2-(3'-pyridyl)-chromone
6-carboxy-8-propyl-2-(2'-pyrazinyl)-chromone
6-carboxy-8-propyl-2-(3'-pyridyl)-chromone
6-carboxy-2-(β-phenyl-vinyl)-chromone
6-carboxy-2-(α-methyl-β-phenyl-vinyl)-chromone
6-carboxy-2-[β-2'-(2-ethoxy-ethoxy)-phenyl-vinyl]-chromone
6-carboxy-2-[β-2'-(2-hydroxy-ethoxy)-phenyl-vinyl]-chromone
6-carboxylic-2[β-2'-(2-hydroxy-propoxy)-phenyl-vinyl]-chromone
6-carboxy-2-[β-2'-(3-hydroxy-propoxy)-phenyl-vinyl]-chromone
6-carboxy-2[β-(2'-pyridyl)-vinyl]-chromone
6-carboxy-2-[β-(3'-pyridyl)-vinyl]-chromone
6-carboxy-2[β-(4'-pyridyl-vinyl]-chromone
7-carboxy-2-[-phenyl-vinyl)-chromone
6-carboxy-2[β-2'-pyrazinyl)-vinyl]-chromone
6-carboxy-flavone
6-carboxy-3'-hydroxy-flavone
6-carboxy-3'-chloro-flavone as well as the pharmaceutically acceptable salts thereof, especially the sodium salts and the hydrochlorides of the esters with diethylaminoethanol and morpholinoethanol as well as the glycolic and pivaloxymethyl esters.

The 5:6-benzo-γ-pyrone derivatives may be prepared by a process comprising:

(a) cyclizing a compound of formula (II)

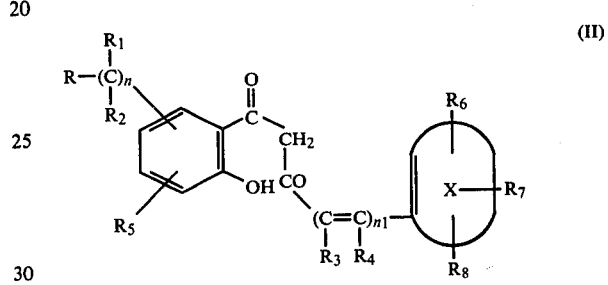

wherein
n, $n_1$, R, $R_1$, $R_2$, $R_3$, $R_4$, $R_5$, $R_6$, $R_7$, $R_8$ and X are as defined above, to obtain compounds of general formula (I) wherein W is

(b) reacting a compound of general formula (III)

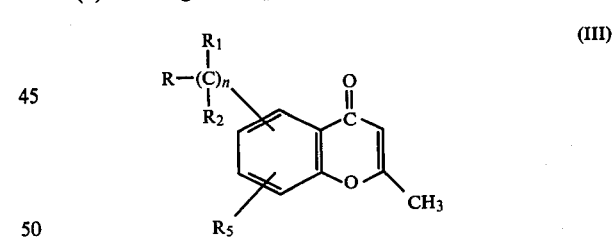

wherein
n, R, $R_1$, $R_2$ and $R_5$ are as hereabove defined, with an aldehyde of general formula (IV)

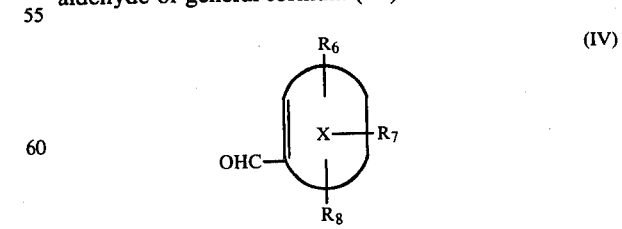

wherein
$R_6$, $R_7$, $R_8$ and X are as hereabove defined, so as to obtain compounds of formula (I) wherein $n_1$ is 1, $R_3$ and $R_4$ are hydrogen, and W is

(c) dehydrogenating a compound of general formula (V)

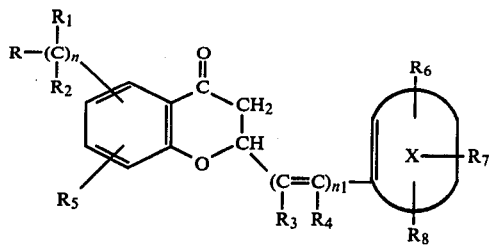

wherein
n, $n_1$, R, $R_1$, $R_2$, $R_3$, $R_4$, $R_5$, $R_6$, $R_7$, $R_8$ and X are as hereabove defined, so as to obtain compounds of general formula (I), wherein W is

(d) dehydrohalogenating a compound of general formula (VI)

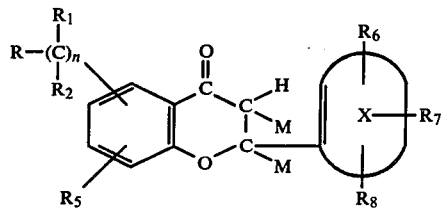

wherein one of M is hydrogen, and the other is halogen, n, R, $R_1$, $R_2$, $R_3$, $R_4$, $R_5$, $R_6$, $R_7$, $R_8$ and X are as hereabove defined, so as to obtain compounds of general formula (I), wherein W is

and $n_1$ is zero;
and, if desired, converting a compound of general formula (I), wherein W is

into a compound of general formula (I), wherein W is

by treatment with a sulphurating agent or, if desired, converting a compound of general formula (I) wherein W is

into a compound of general formula (I) wherein W is

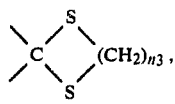

wherein $n_3$ is 2 or 3, by reaction with a compound of formula HS—$(CH_2)_{n3}$—SH, and/or, if desired, converting a compound of general formula (I) into another compound of general formula (I) by known methods, and/or if desired, converting a compound of general formula (I) into a pharmaceutically acceptable salt thereof; and/or, if desired, resolving an obtained mixture of optical isomers into the different isomers.

The cyclisation of the compound of formula (II) is preferably performed in presence of acid catalysts, such as, for example, hydrochloric acid, hydroiodic acid, sulphuric acid, formic aicd, at a temperature ranging preferably between 20° and 120° C. and in an inert solvent selected for instance from the group consisting of methanol, ethanol, dioxane, tetrahydrofuran, benzene, toluene, acetic acid and their mixtures. The reaction of a compound of formula (III) with the aldehyde of formula (IV) is carried out in the presence of basic condensing agents, such as, for example, sodium ethoxide, sodium methoxide, sodium hydride, sodium amide, sodium or potassium hydroxide, at a temperature ranging preferably between 0° and 100° C. and in a solvent preferably selected from the group consisting of methanol, ethanol, dioxane, water and their mixture.

The dehydrogenation of the compound of general formula (V) is preferably performed with $SeO_2$ in organic solvents, such as, for instance, toluene, xylene or n-amyl alcohol and at reflux temperature. The dehydrohalogenation of the compound of formula (VI) is preferably carried out by treatment with a base preferably selected from the group consisting of NaOH, KOH, $K_2CO_3$, potassium tert.-butylate, pyridine, triethylamine, in an organic solvent selected for example from the group consisting of ethanol, acetone, dimethylformamide and dimethylsulphoxide, at a temperature ranging between the room temperature and the reflux temperature.

The optional conversion of a compound of general formula (I) wherein W is

into a compound of general formula (I) wherein W is

may be effected by treatment with $P_2S_5$, at the reflux temperature, of a solution of the compound of general formula (I) wherein W is

in an inert organic solvent, such as, benzen, dioxane, tetrahydrofuran, and their mixtures.

The optional conversion of a compound of general formula (I) wherein W is

into a compound of general formula (I) wherein W is

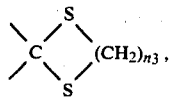

by reaction with a compound of formula HS—$(CH_2)_{n3}$—SH is preferably carried out in presence of an acid catalyst, such as, for instance, p-toluenesulphonic acid, pyridine hydrochloride, $ZnCl_2$, $BF_3$ etherate in an inert solvent, such as, e.g. benzene or toluene, or also in absence of solvents at temperatures varying between 20° and 120° C.

A compound of general formula (I) may be converted, as hereabove stated, into another compound of general formula (I) by known methods.

For example, a compound of general formula (I) wherein R is a cyano group may be converted into a compound of general formula (I) wherein $R_1$ is a carboxy group by acid hydrolysis, for instance, with hydrochloric or sulphuric acid. Likewise, a compound of general formula (I) wherein R is a carboxy group may be converted into a compound of general formula (I) wherein R is a carbalkoxy group by esterification, for example, by reaction of the alkaline salt of the acid with the desired alkyl halide.

Free hydroxy groups may be also etherified by treatment for instance with alkyl halides or etherified hydroxy groups may be converted into free hydroxy groups for example by treatment with a pyridine salt, preferably hydrochloride, or with a strong acid or a Lewis acid.

In a compound of formula (I) wherein X is a nitrogen containing heteromonocyclic radical, a nitrogen atom may be converted into the corresponding N-oxide by oxidation, e.g., with peracids, such as, peracetic, permaleic and perbenzoic acid.

A compound of formula (I) wherein R is a carboxy group may be converted into a compound of formula (I) wherein R is the tetrazolyl radical of formula

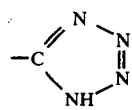

by known methods, for example, by converting the carboxy group into the corresponding halide, preferably chloride, e.g., by reaction with thionyl chloride in benzene at reflux temperature, then, reacting the halide, e.g. with ammonia, to give the corresponding amide, dehydrating the amide to nitrile, for example by means of p-toluenesulphonylchloride in pyridine, and finally, reacting the nitrile with sodium azide and ammonium chloride in dimethylformamide at a temperature varying between room temperature and 100° C.

Also the optional salification of the compounds of formula (I) may be performed according to conventional methods.

The compounds formula (II) may be prepared by reacting a compound of formula (VII)

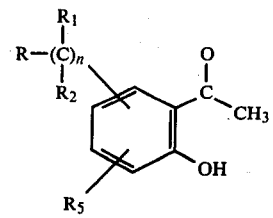

wherein
n, R, $R_1$, $R_2$, $R_5$ are as above defined, with a compound of formula (VIII)

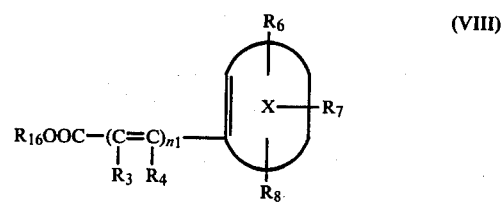

wherein
$n_1$, $R_3$, $R_4$, $R_6$, $R_7$, $R_8$ and X are as above defined and $R_{16}$ is aryl, preferably phenyl, or alkyl.

The reaction between the compound of formula (VII) and the compound of formula (VIII) is preferably effected in an organic solvent such as e.g. methanol, ethanol, dioxane and pyridine, in presence of a strong base, such as, for instance, sodium methoxide, sodium ethoxide, sodium hydride and at a temperature ranging between the room temperature and the reflux temperature. An alternative method to prepare the compounds of formula (II) consists in reacting by known methods a compound of formula (VII) with a compound of formula (IX)

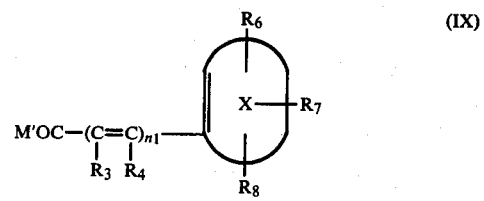

wherein
M' is halogen or hydroxy, and $n_1$, $R_3$, $R_4$, $R_6$, $R_7$, $R_8$ and X are as previously defined, to obtain a compound of formula (X)

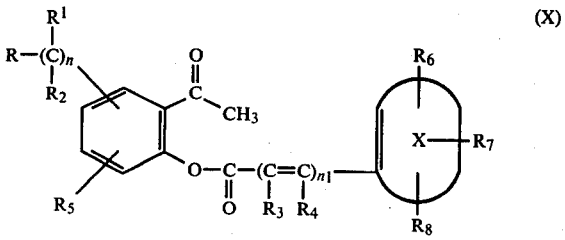

wherein
n, $n_1$, R, $R_1$, $R_2$, $R_3$, $R_4$, $R_5$, $R_6$, $R_7$, $R_8$ and X are as above defined, and submitting then the compounds of formula (X) to a rearrangement which is carried out in an inert solvent, for example, pyridine, toluene, methylethyl-ketone, in presence of a strong base, e.g., sodium, sodium amide, potassium hydroxide, potassium carbonate, at a temperature varying between the room and the reflux temperature.

The compounds of formula (III) may be prepared, for instance, by acid cyclization of β-diketones of general formula (XI)

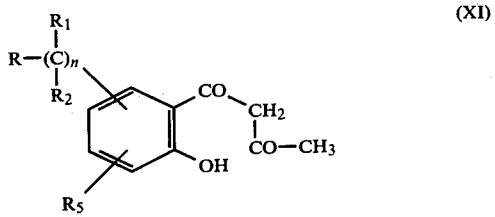

wherein n, R, $R_1$, $R_2$, $R_5$ are as above defined, which in turn may be obtained by basic condensation of an acetic ester, such as, for example, methylacetate, ethylacetate, phenylacetate with a substituted orthohydroxyacetophenone of general formula (VII), preferably carrying out the reaction at a temperature ranging between 20° and 100° C., in absence of solvents or in a solvent preferably selected from the group consisting of benzone, toluene, dioxane and their mixtures, using, e.g. sodium hydride as condensing agent.

The compounds of formula (VII) may be prepared for example starting from the appropriate substituted phenols by a Friedel-Crafts condensation or by a Fries re-arrangement.

The compounds of formula (V) may be prepared starting from the compounds of formula (XII)

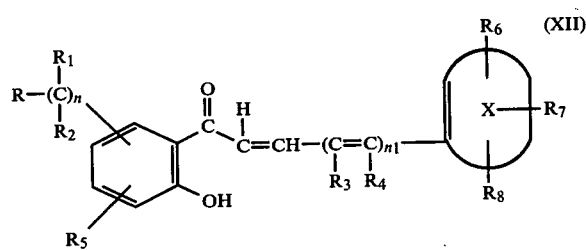

wherein n, $n_1$, R, $R_1$, $R_2$, $R_3$, $R_4$, $R_5$, $R_6$, $R_7$, $R_8$, and X are as hereabove defined, by reaction with basic condensing agents, such as sodium or potassium hydroxide, sodium amide, sodium hydride, sodium or potassium carbonate, potassium acetate, or acids, for example, hydrohalic acids, sulphuric, phosphoric, p-toluenesulphonic acid in a solvent e.g. preferably selected from the group consisting of methanol, ethanol, dioxane, tetrahydrofuran, benzene, toluene, dimethylsulphoxide at a temperature varying between the room and reflux temperature.

The compounds of formula (XII) may be in turn prepared by condensing a compound of formula (VII) with a substituted aldehyde of formula (XIII)

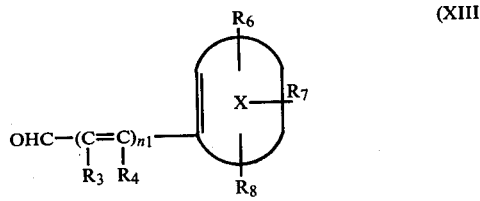

wherein $n_1$, $R_3$, $R_4$, $R_6$, $R_7$, $R_8$, and X are as previously defined.

The condensation may be carried out in a solvent, selected for example from the group consisting of methanol, ethanol, dioxane, water and their mixture, and in presence of a basic catalyst, such as, piperidine, sodium hydroxide, sodium hydride, sodium alkoxide, and at a temperature ranging between the room and the reflux temperature.

The compounds of formula (VI) may be prepared by halogenation for example with N-bromosuccinimide or pyridine perbromide [(N.B. Lorotte et al., J. Org. Chem. 16, 930 (1951); S. Hishide et al., J. Chem. Soc. Japan 74, 697 (1953)] of the compounds of formula (V).

The compounds of the invention possess anti-allergic activity, as is shown by the fact that they are active in the passive cutaneous anaphylaxis (PCA) test in rats, according to Goose Y. and Blair A.M.Y.N. (Immunology, 1969, 16:749). They can be therefore used in prevention and treatment of bronchial asthma, allergic rhinitis, hay fever, urticaria and dermatosis. It is to be noted that in comparison either with the prior art compounds already known as antiallergic agents or with the compounds excluded from the scope of general formula (I), as before reported, e.g., 6-carboxy-flavone 6-carboxy-4'-hydroxy-flavone, and 6-carboxy-3'-chloro-flavone, then new compounds of the invention, in particular the preferred compounds mentioned in the paragraph bridging page 4 and page 5, offer the important and unexpected advantage, when orally administered, of being far more active as antiallergic agents, and of allowing to obtain a far more protracted duration of antiallergic activity.

The following Table shows the protection obtained with the compounds of this invention when orally given, in PCA test in rats, compared with wo well-known anti-allergic drugs, i.e., disodium cromoglycate (DSCG) and AH 7725, i.e., 2-carboxy-7-hydroxyethoxy-xanthons (Fullarton, J., Martin, L. E., and Vardey, C., Int. Arch. All., 1973, 45: 84).

TABLE

| Compound | Dosage [mg/kg/p.o.] | % Inhibition In Comparison With Controls At Various Times Of Pretreatment | | | |
|---|---|---|---|---|---|
| | | 15 min. | 30 min. | 60 min. | 120 min. |
| DSCG | 50 | 6.0 | 5.5 | 3.2 | 2.5 |
| AH 7725 | 50 | 42.6 | 14.4 | 13.3 | 3.8 |
| 6-carboxy-2'-isopropoxy-flavone | 50 | 82.9 | 39.5 | 27.6 | 24.4 |
| 6-carboxy-2-(β-phenyl-vinyl)-chromone | 50 | 69.9 | 45.8 | 19.6 | 16.6 |
| 6-carboxy-2-(2'-pyrasinyl)-chromone | 50 | 87.0 | 47.3 | 31.9 | 26.3 |
| 6-carboxy-flavone | 50 | 32.1 | 23.5 | 6.8 | 3.4 |
| 6-carboxy-4'-hydroxy-flavone | 50 | 9.2 | 4.0 | 3.7 | 3.9 |
| 6-carboxy-3'-chloro-flavone | 50 | 31.0 | 22.3 | 5.9 | 2.1 |

In addition to anti-allergic activity, the compounds of this invention are effective in decreasing the airway resistance and in increasing pulmonary compliance, and can be therefore used for the treatment of respiratory insufficiency, such as, for example, acute pulmonary insufficiency, as shown by the results obtained in rats using the technique described by Palecek F., Palecekova M., and Aviado D. M. (Arch. Environ. Health, 1967, 15: 332–342). In these experiments, the compounds of the invention, in particular, 6-carboxy-2'-isopropoxy-flavone, lower the airway resistance and increase pulmonary compliance even at a dosage as low as 3 mg/kg/i.v.; at the same dosage, they are successful in antagonizing (50%) the bronchoconstrictive effect of 5-HT (=5-hydroxy-triptamine, i.e. serotonin) and of the compound 48/80 (histamine releasing drug).

The compounds of the present invention furthermore possess anti-ulcer activity, as demonstrated by the fact that they proved to be active in inhibiting stress-induced ulcers in rats undergoing restraint in a water bath at 25° for 40 minutes according to a modification of the technique described by Takagi, K. and Okabe, S. (Jap. J. of Pharmac., 1968, 18:9).

In this experiment, the compounds of the invention, in particular, 6-carboxy-2'-isopropoxy-flavone sodium salt, show at 45% inhibition of the stress-induced ulcers in rats, when administered at a dosage of 50 mg/kg/i.v..

The compounds of the invention be administered in conventional manner, for instance, orally and parenterally at a daily dosage preferably of 0.5 to 15 mg/kg, or by inhalation, preferably at a daily dosage of 0.5 to 100mg, preferably 0.5 to 25 mg, or by topical application.

The nature of the pharmaceutical compositions containing the compounds of this invention in association with pharmaceutically acceptable carriers or diluents will, of course, depend upon the desired mode of administration.

The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, or creams, or lotions for topical used.

Thus, for oral administration, the pharmaceutical compositions containing the compounds of this invention, are preferably tablets, pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as, for example, starches, gelatine, methylcellulose, carboxymethylcellulose, gum-arabic, tragacanth, polyvinylpyrrolidone, disintegrating agents, such as, for instance, starches, alginic acid, alginates, sodium starch glycolate; effervescing mixtures; dyestuffs; sweeteners; wetting agents, such as, for instance, lecithin, polisorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or filmcoating processes.

For the treatment of allergic asthma, the compounds of the invention are also administered by inhalation. For such use, suitable compositions may comprise a suspension or solution of the active ingredient, preferably in the form of a salt, such as the sodium salt, in water, for administration by means of a conventional nebulizer. Alternatively, the compositions may comprise a suspension or a solution of the active ingredient in a conventional liquified propellant, such as, dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g., lecithin. The compounds of the invention may also be administered in the form of powders by means of a suitable insufflator device and in this case the fine particle sized powders of the active ingredient may be mixed with a diluent material such as lactose.

Furthermore, the compounds of this invention may also be administered by intradermal or intravenous injection in the conventional manner.

In addition to the internal administration, the compounds of this invention may find use in compositions for topical application, e.g. as creams, lotions or pastes for use in dermatological treatments. For these compositions the active ingredient may be mixed with conventional oleaginous or emulsifying excipients.

The following examples illustrate but do not limit the present invention.

EXAMPLE 1

A solution consisting of methyl 3-acetyl-4-hydroxy-benzoate (60 g) and methyl 2-isopropoxy-benzoate (120 g) in dioxane (400 ml) was slowly added under stirring at room temperature to a suspension of sodium hydride 50% (45 g) in dioxane (200 ml). The mixture was kept for 4 hours at 80° C., cooled, then diluted with petroleum ether (600 ml), and subsequently filtered. The collected precipitate was dissolved in water, acidified with acetic acid and extracted with ethylacetayte. The organic phase was washed with potassium carbonate 5% and water, then evaporated to dryness and crystallized from ethanol to give (2-hydroxy-5-carbomethoxy-benzoyl)-(2-isopropoxy-benzoyl)-methane (70 g); m.p. 105°–107° C.) which was then refluxed for 15 minutes with formic acid 99% (280 ml). After cooling and dilution in water (one liter) and filtration, the collected precipitate was crystallised from acetone to obtain 6-carbomethoxy-2'-isopropoxy-flavone (60 g; m.p. 154°–155° C.), which was hydrolysed with a solution of potassium hydroxide 1% (1. 1,020) in ethanol 95% at reflux temperature for 30 minutes. The mixture was cooled, acidified with acetic acid, concentrated under vacuum to obtain a precipitate, which was filtered, washed with ethanol (95%) and water to give, after crystallisation from ethanol, 6-carboxy-2'-isopropoxy-flavone (45 g; m.p. 209°–211° C.).

By proceeding analogously, the following compounds were obtained:

6-carboxy-2'-propoxy-flavone, m.p. 201°–203° C.;
6-carboxy-2'-(2-methyl-propoxy)-flavone, m.p. 193°–195° C.;
6-carboxy-2'-butoxy-flavone, m.p. 204°–206° C.;
6-carboxy-2'-ethoxy-flavone, m.p. 225°–227° C.;
6-carboxy-2'-methoxy-flavone, m.p. 265°–267° C.;
6-carboxy-2',6'-dimethoxy-flavone, m.p. >300° C.;
6-carboxy-2'-(1-methyl-propoxy)-flavone;
6-carboxy-flavone; m.p. 301°–303° C.
6-carboxy-3'-chloro-flavone, m.p. 281°–283° C.

EXAMPLE 2

A solution of methyl 3-acetyl-4-hydroxy-benzoate (54 g) and methyl 2-benzyloxy-benzoate (135 g) in dioxane (400 ml) was slowly added under stirring at room temperature to a suspension of sodium hydride 50% (40 g) in dioxane (150 ml). The mixture was kept for 5 hours at 70° C., then cooled and diluted with petroleum ether, and subsequently filtered. The collected precipitate was dissolved in water, acidified with acetic acid and extracted with ethylacetate. The organic phase was washed with potassium carbonate 5% and water, then evaporated to dryness. After crystallisation from methanol, (2-hydroxy-5-carbomethoxy-benzoyl)--(2-benzyloxy-benzoyl)-methane (74 g; m.p. 95°–97° C.) was obtained, which was then refluxed for 24 hours with formic acid 99% (500 ml). After cooling and dilution with ethanol (500 ml), the precipitate obtained was filtered and washed with ethanol to give 6-carbomethoxy-2'-hydroxy-flavone (31 g; m.p. 290°–291° C.) which was then reacted in dimethylformamide (150 ml) with 1-chloro-2-benzoyloxy-propane (26 g) and potassium carbonate (18 g) at 70° C. for 16 hours. The mixture was cooled, diluted in water (600 ml), filtered, then washed with water to obtain 6-carbomethoxy-2'-(2-benzoyloxy-propoxy)-flavone (45 g), which was hydrolysed with a solution of potassium hydroxide 1% (1. 1,250) in ethanol (95%) at reflux temperature for an hour. After cooling, acidification with acetic acid, concentration to small volume under vacuum and dilution in water, the precipitate obtained was filtered, then washed with water to give, after crystallisation with methylene chloride/ethylacetate, 6-carboxy-2'-(2-hydroxy-propoxy)-flavone (18.5; m.p. 211°–213° C.

By proceeding analogously, the following compounds were obtained:

6-carboxy-2'-(2-hydroxy-ethoxy)-flavone, m.p. 238°–240° C.
6-carboxy-2'-(3-hydroxy-propoxy)-flavone
6-carboxy-2'-(2-hydroxy-3-methyl-butoxy)-flavone
6-carboxy-3'-hydroxy-flavone, m.p. 321°–323° C.
6-carboxy-4'-hydroxy-flavone, m.p.>300° C.

EXAMPLE 3

6-carbomethoxy-2'-hydroxy-flavone (5 g), obtained according to the method described in Example 2, was reacted in dimethylformamide (30 ml) with β-ethoxy-ethyl-bromide (3.5 g) and potassium carbonate (3.2 g) at 80° C.) for 16 hours. The mixture was cooled, diluted in water, filtered, washed with water. After crystallisation from methanol, 6-carbomethoxy-2'-(2-ethoxyethoxy)-flavone (4.5 g) was obtained, which was hydrolysed with a solution of potassium hydroxide 1% (90 ml) in ethanol 95% at reflux temperature for 45 minutes. Subsequently, after cooling, acidification with acetic acid, concentration, dilution with water, filtration, and crystallisation from ethanol, 6-carboxy-2'-(2-ethoxy-ethoxy)-flavone (3.1 g; m.p. 198°–200° C.) was obtained.

By using the suitable alkyl halides, the following compounds were prepared:

6-carboxy-2'-isopropoxy-flavone, m.p. 208°–210° C.;
6-carboxy-2'-(2-methyl-propoxy)-flavone, m.p. 192°–194° C.;
6-carboxy-2'-(2-hydroxy-propoxy)-flavone, m.p. 210°–212° C.;
6-carboxy-2'-(1-methyl-propoxy)-flavone;
6-carboxy-2'-(2-hydroxy-2-methyl-propoxy)-flavone;
6-carboxy-2'-(2-hydroxy-2-methyl-butoxy)-flavone;
6-carboxy-2'-(2,3-dihydroxy-propoxy)-flavone.

EXAMPLE 4

A mixture consisting of 6-carbomethoxy-2'-hydroxy-flavone (10 g), obtained according to the method described in Example 2, and 1,2-epoxy-butane (6 g) and benzyl-trimethylammonium hydroxide (0.5 ml) in dioxane (40 ml) was kept at reflux temperature for 48 hours. After cooling, dilution with water, and extraction with ethylacetate, the organic phase was washed with potassium carbonate 5% and water. The solution was evaporated to dryness, and the resulting product was treated with the stoichiometric quantity of a solution of potassium hydroxide 1% in ethanol 95% at reflux temperature for an hour. After acidification with acetic acid, concentration under vacuum, dilution with water, filtration and double crystallisation from ethanol, 6-carboxy2'-(2-hydroxy-butoxy)-flavone (4.7 g) was obtained.

EXAMPLE 5

Methyl 3-acetyl-4-cinnamoyloxy-benzoate (46.2 g; m.p. 97°–99° C.) was dissolved in methyl-ethyl-ketone (350 ml). After addition of anhydrous potassium carbonate (37 g), the mixture was refluxed for 6 hours. After cooling, dilution with petroleum ether (500 ml) and filtration, the collected precipitate was dissolved in water, acidified with acetic acid, extracted with ethylacetate. The organic phase was washed with potassium carbonate 5% and water, then evaporated to dryness. After crystallisation from methanol, (2-hydroxy-5-carbomethoxy-benzoyl)-cinnamoyl-methane (31.2 g; m.p. 138°–140° C.) was obtained, which was refluxed for 15 minutes with formic acid 99% (140 ml). After cooling, dilution with water (1. 1 ) and filtration, the collected precipitate was crystallised from acetone to obtain 6-carbomethoxy-2-(β-phenylvinyl)-chromone (27.8 g; m.p. 175°–177° C.) which was hydrolysed with a solution of potassium hydroxide 1% (600 ml) in ethanol 95% at reflux temperature for 45 minutes. After cooling, acidification with acetic acid, concentration under vacuum and dilution with water, the precipitate was collected and washed with water to give, after crystallisation from acetone, 6-carboxy-2-(β-phenyl-vinyl)-chromone (16.1 g; m.p. 273°–275° C.).

By using the suitable esters of methyl 3-acetyl-4-hydroxy-benzoate, the following compounds were prepared:

6-carboxy-2-(α-methyl-β-phenyl-vinyl)-chromone, m.p. 220°–222° C.;
6-carboxy-2-(β-2'-methoxyphenyl-vinyl)-chromone, m.p. 270° C.(dec.);
6-carboxy-2-[β-(2'-pyridyl)-vinyl]-chromone;
6-carboxy-2-[β-(3'-pyridyl)-vinyl]-chromone;
6-carboxy-2-[β-(4'-pyridyl)-vinyl]-chromone;
6-carboxy-2-[β-(2'furyl)-vinyl]-chromone.

EXAMPLE 6

By using the method described in Example 5, starting from methyl 3-acetyl-4-(ortho-benzoyloxy-cinnamoyloxy)-benzoate, and hydrolysing the benzylether group by heating at reflux temperature for 24 hours with an excess of formic acid 99%, 6-carbomethoxy-2-(β-2'hydroxyphenyl-vinyl)-chromone was obtained (m.p. 252°–254° C.), after crystallization from acetone.

This product (7 g), dissolved in dimethylformamide (35 ml) was reacted with β-ethoxy-ethyl-bromide (4.2 g) and anhydrous potassium carbonate (4 g at 70° C. for 24 hours. After cooling, dilution with water and filtration, the collected precipitate was hydrolyzed with the stoichiometric quantity of potassium hydroxide 1% in ethanol 95% at reflux temperature for an hour. After cooling, dilution with water, acidification with citric acid, the precipitate was collected, and crystallised from methanol/benzene, to obtain 6-carboxy-2-[β-2'-(2-ethoxy-ethoxy)-phenyl-vinyl]-chromone (3.6 g; m.p. 218° C. dec.).

By using the suitable alkyl halides, the following compounds were obtained:

6-carboxy-2-[β-2'-(2-hydroxy-propoxy)-phenyl-vinyl]-chromone;
6-carboxy-2-[β-2'-(3-hydroxy-propoxy)-phenyl-vinyl]-chromone;
6-carboxy-2-[β-2'-(2-hydroxy-ethoxy)-phenyl-vinyl]-chromone.

EXAMPLE 7

A solution consisting of methyl 3-acetyl-4-hydroxy-benzoate (16 g) and methyl nicotinate (23 g) in dioxane (100 ml) was slowly added at room temperature under stirring to a suspension of sodium hydride 50% (12 g) in dioxane (60 ml). The solution was kept for 6 hours at 80° C., then cooled, diluted with petroleum ether (200 ml), and filtered. The product obtained was dissolved in water and treated with acetic acid; the precipitate obtained was washed with water and crystallised with methylene chloride/methanol to give (2-hydroxy-5-carbomethoxy-benzoyl)-nicotinoylmethane (17.2 g; m.p. 200°-202° C.) which was then treated with ethanol (300 ml) containing concentrated hydrochloric acid 1% at reflux temperature for 2 hours. After concentration under vacuum, dilution with water, neutralisation with sodium acetate, the precipitate was filtered. The raw 6-carbomethoxy-2-(3'-pyridyl)-chromone (15.1 g) was hydrolysed with the stoichiometric quantity of potassium hydroxide 1% in ethanol 95% at reflux temperature for an hour. After cooling, dilution with water (600 ml), neutralisation with acetic acid, the precipitate was collected, to obtain, after crystallisation from dimethylformamide, 6-carboxy-2-(3'-pyridyl)-chromone (9.8 g; m.p.>350° C.); I.R. (KBr): $\nu_{C=O}$(carboxy) 1680 cm$^{-1}$, $\nu_{C=O}$(chromone) 1630 cm$^{-1}$, 1610 cm$^{-1}$, $\gamma_{C-H}$ (meta-substituted pyridine) 770 cm$^{-1}$, 696 cm$^{-1}$.

By proceeding analogously, the following compounds were prepared:

6-carboxy-2-(2'-pyridyl)-chromone, m.p.>300° C.; I.R. (KBr): $\nu_{C=O}$ (carboxy 1710 cm$^{-1}$, $\nu_{C=O}$(chromone) 1650 cm$^{-1}$, $\gamma_{C-H}$(ortho-substituted pyridine) 768 cm$^{-1}$;
6-carboxy-2-(4'-pyridyl)-chromone, m.p.>350° C.; I.R. (KBr): $\nu_{C=O}$(carboxy) 1690 cm$^{-1}$, $\nu_{C=O}$(chromone) 1630 cm$^{-1}$, $\gamma_{C-H}$ (para-substituted pyridine) 825 cm$^{-1}$;
6-carboxy-2-(2'-thienyl)-chromone, m.p. 301°-304° C.;
6-carboxy-2-(2'-furyl)-chromone, m.p. 330°-332° C.;
6-carboxy-2-(2'-pyrazinyl)-chromone, m.p.>350° C.; I.R. (KBr): $\nu_{C=O}$(carboxy) 1695 cm$^{-1}$, $\nu_{C=O}$(chromone) 1645 cm$^{-1}$;
6-carboxy-2-(2'-imidazolyl)-chromone;
6-carboxy-2-(5'-imidazolyl)-chromone;
6-carboxy-2-[2'-(2-methyl-propoxy)-3'-pyridyl]-chromone;
6-carboxy-2-[2'-(1-methyl-propoxy)-3'-pyridyl]-chromone;
6-carboxy-2-(2'-isopropoxy-3'-pyridyl)-chromone;
6-carboxy-2-(2'-butoxy-3'-pyridyl)-chromone;
6-carboxy-2-[2'-(3-methyl-butoxy)-3'-pyridyl]-chromone;
6-carboxy-2-(2'-pentyloxy-3'-pyridyl)-chromone;
6-carboxy-2-[3'-(2-methyl-propoxy)-2'-pyridyl]-chromone;
6-carboxy-2-[3'-(1-methyl-propoxy)-2'-pyridyl]-chromone;
6-carboxy-2-(3'-isopropoxy-2'-pyridyl)-chromone;
6-carboxy-2-(3'-pentyloxy-2'-pyridyl)-chromone;
6-carboxy-2-[3'-(3-methyl-butoxy)-2'-pyridyl]-chromone;
6-carboxy-2-3'-(2-hydroxy-propoxy)-2'-pyridyl-chromone;
6-carboxy-2-(4'-isopropoxy-3'-pyridyl)-chromone;
6-carboxy-2-[4'-(2-methyl-propoxy)-3'-pyridyl]-chromone;
6-carboxy-2-[4'-(1-methyl-propoxy)-3'-pyridyl]-chromone;
6-carboxy-2-[4'-(1-methyl-butoxy)-3'-pyridyl]-chromone.

EXAMPLE 8

By using the method described in Example 7, starting from methyl 3-hydroxy-4-acetyl-benzoate, the following compounds were obtained:

7-carboxy-2-(2'-pyridyl)-chromone;
7-carboxy-2-(3'-pyridyl)-chromone;
7-carboxy-2-(2'-furyl)-chromone;
7-carboxy-2-(2'-pyrazinyl)-chromone;
7-carboxy-2-[2'-(2-methyl-propoxy)-3'-pyridyl]-chromone;
7-carboxy-2-[2'-(1-methyl-propoxy)-3'-pyridyl]-chromone;
7-carboxy-2-(2'-isopropoxy-3'-pyridyl)-chromone;
7-carboxy-2-(2'-butoxy-3'-pyridyl)-chromone;
7-carboxy-2-[2'-(3-methyl-butoxy)-3'-pyridyl]-chromone;
7-carboxy-2-[3'-(2-methyl-propoxy)-2'-pyridyl]-chromone;
7-carboxy-2-[3'-(1-methyl-propoxy)-2'-pyridyl]-chromone;
7-carboxy-2-(3'-isopropoxy-2'-pyridyl)-chromone;
7-carboxy-2-(3'-pentyloxy-2'-pyridyl)-chromone;
7-carboxy-2-[3'-(3-methyl-butoxy)-2'-pyridyl]-chromone.

EXAMPLE 9

By proceeding according to Example 1, starting from methyl 3-acetyl-4-hydroxy-benzoate and from the proper methyl N-alkyl and N,N-dialkylantranilate, the following compounds were obtained:
6-carboxy-2'-methylamino-flavone;
6-carboxy-2'-isopropylamino-flavone;
6-carboxy-2'-dimethylamino-flavone;
6-carboxy-2'-(N-methyl-N-isopropyl-amino)-flavone;
6-carboxy-2'-(N-methyl-N-ethyl-amino)-flavone.

EXAMPLE 10

By proceeding according to Examples 2 and 3, starting from the intermediates methyl 3-acetyl-4-hydroxy-5-allyl-benzoate (m.p. 106°-108° C.) and methyl 3-acetyl-4-hydroxy-5-propyl-benzoate (m.p. 89°–91° C.), prepared according to the method described in J. Pharm. Soc. Japan, 74, 47 (1954), the following compounds were obtained:

6-carboxy-8-propyl-2'-isopropoxy-flavone, m.p. 205°–207° C.;
6-carboxy-8-allyl-2'-(2-hydroxy-propoxy)-flavone;
6-carboxy-8-propyl-2'-(2-hydroxy-propoxy)-flavone.

EXAMPLE 11

By using the methods described in Example 7, starting from the same intermediates as in Example 10, the following compounds were prepared:

6-carboxy-8-allyl-2-(3'-pyridyl)-chromone, m.p. 318°–323° C.;
6-carboxy-8-propyl-2-(3'-pyridyl)-chromone;
6-carboxy-8-allyl-2-(2'-pyrazinyl)-chromone;
6-carboxy-8-propyl-2-(2'-pyrazinyl)-chromone;

EXAMPLE 12

To a solution consisting of 2-methyl-6-carbethoxy-chromone (5 g) and 3-pyridyl-carboxy aldehyde (5.5 g) in absolute ethanol (100 ml) a solution of sodium (0.5 g) in ethanol (50 ml) was slowly added under stirring at 0° C. The mixture was kept for 2 hours at room temperature, then acidified with acetic acid, concentrated under vacuum, diluted with water, and finally, the precipitate was collected, to give, after crystallisation from methanol, 6-carbomethoxy-2-(β-3'-pyridyl-vinyl)chromone (3.8 g; m.p. 170°–180° C.), which was hydrolysed with the stoichiometric amount of a solution of potassium hydroxide 1% in ethanol 95% at reflux temperature for an hour. After cooling, dilution with 10% aqueous monobasic sodium phosphate allowed to obtain a precipitate, which was collected by filtration and crystallized from N,N-dimethylformamide/methanol to give 6-carboxy-2-(β-3'-pyridyl-vinyl)-chromone (1.8 g; m.p.>350° C.); I.R. (KBr): $\nu_{C=O}$(carboxy) 1710 cm$^{-1}$, $\nu_{C=O}$(chromone) 1655 cm$^{-1}$, 1640 cm$^{-1}$, γ

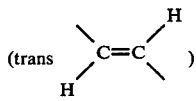

(trans)

970 cm$^{-1}$.

By proceeding analogously, the following compounds were obtained:

6-carboxy-2-(β-2'-pyridyl-vinyl)-chromone
6-carboxy-2-(β-4'-pyridyl-vinyl)-chromone
6-carboxy-2-(β-2'-furyl-vinyl)-chromone.

EXAMPLE 13

Piperidine (200 m) was added to a solution consisting of methyl 3-hydroxy-4-acetyl-benzoate (15 g) and salicylaldehyde (15 g) in absolute ethanol (400 ml); the mixture was kept at reflux temperature for 40 hours. After cooling, acidification with hydrochloric acid and extraction with ethylacetate, the organic phase was washed with K$_2$CO$_3$ 5%, and with water, then evaporated to dryness. The residue, so obtained (11 g), was dissolved in n-amylic alcohol (200 ml) by adding SeO$_2$ (11 g) and the solution was kept at reflux temperature for 18 hours. After cooling, the residue was filtered off and the amylic alcohol was distilled in a steam current: the residue of the distillation was recovered by extraction with chloroform, to give, after crystallisation from ethanol, 7-carbomethoxy-2'-hydroxy-flavone (6.3 g), which was reacted in dimethylformamide (30 ml) with 2-bromo-propane (3.5 g) and anhydrous potassium carbonate (4 g) at 70° C. for 18 hours. After cooling, the mixture was diluted with water (200 ml), and then filtered, so obtaining 7-carbomethoxy-2'-isopropoxy-flavone (7.9 g) which was subsequently hydroylsed by treatment with the stoichiometric quantity of a solution of potassium hydroxide 1% in ethanol 95% at reflux temperature for 30 minutes. After cooling, acidification with acetic acid, dilution with water, filtration, and subsequent crystallisation from ethanol, 7-carboxy-2'-isopropoxy-flavone (5.7 g) was obtained.

By proceeding analogously, by using the proper alkyl halides, the following compounds were obtained:

7-carboxy-2'-(2-methyl-propoxy)-flavone;
7-carboxy-2'-(1-methyl-propoxy)-flavone;
7-carboxy-2'-(2-hydroxy-propoxy)-flavone;
7-carboxy-2'-(2-ethoxy-ethoxy)-flavone.

EXAMPLE 14

A mixture consisting of ethyl 3-acetyl-4-hydroxy-benzoate (6 g) and 2-nitro-benzaldehyde (5 g) dissolved in ethanol (100 ml) and piperidine (100 ml) was kept at reflux temperature for 24 hours. The mixture was then cooled, diluted in water (800 ml), acidified with hydrochloric acid, extracted with ethylacetate, washed with water and evaporated to dryness to obtain as raw product, 6-carbomethoxy-2'-nitro-flavanone. This product (6.8 g) was dissolved in chloroform (40 ml) and treated with a solution of benzoyl peroxide (0.15 g) and N-bromosuccinimide (3.8 g) dissolved in chloroform (60 ml). The mixture was kept at reflux temperature for 4 hours, then evaporated to dryness under vacuum at low temperature; then the residue, dissolved in thanol 95% (150 ml), was treated with sodium hydrate 4 N (25 ml) at room temperature for a night. After acidification with hydrochloric acid and filtration, 6-carboxy-2'-nitro-flavone (3.7 g) was obtained, which was subsequently treated with stannous chloride (20 g) in concentrated hydrochloric acid (15 ml) and glacial acetic acid (15 ml) at reflux temperature for 4 hours. After cooling, dilution with water, neutralisation with ammonium hydrate 28 Be, the precipitate was filtered to give, after crystallisation from dimethylformamide, 6-carboxy-2'-amino-flavone (1.8 g; m.p. > 300° C.).

EXAMPLE 15

6-carboxy-2-(3'-pyridyl)-chromone (10 g) suspended in acetic acid (500 ml) was treated with hydrogen peroxide 36% (100 ml) at reflux temperature for 24 hours. After cooling, dilution with water and filtration, the collected precipitate was crystallised from dimethylformamide to obtain 6-carboxy-2-(3'-pyridyl-N-oxide)-chromone (5.7 g; m.p. > 320° C.) I.R. (KBr): $\nu_{C=O}$ (carboxy) 1700 cm$^{-1}$, $\nu_{C=O}$(chromone) 1650 cm$^{-1}$, $\nu_{N\rightarrow O}$ 1280 cm$^{-1}$.

By proceeding analogously, the following compounds were obtained:

6-carboxy-2-(2'-pyridyl-N-oxide)-chromone
6-carboxy-2-(4'-pyridyl-N-oxide)-chromone

EXAMPLE 16

6-carboxy-2'-isopropoxy-flavone (21 g) suspended in 1,2-dichloroethane (75 ml) was treated with thionyl chloride (6 ml) at reflux temperature for an hour. The solution was then cooled and ammonium hydrate 28 Be (15 ml) was added under vigorous stirring. An hour later, after dilution with ethylether (300 ml) and filtration, 6-carboxamide-2'-isopropoxy-flavone (21 g; m.p. 267°–270° C.) was obtained which was treated with p-tolunesulphonylchloride (37.5 g) in pyridine (33 ml) and dimethylformamide (160 ml) at 90° C. for 8 hours. After cooling, dilution with water (1.1.5) and filtration, the collected precipitate was dried and washed with hot isopropylether (300 ml), to give 6-cyano-2'-isopropoxy-flavone (15.6 g; m.p. 172°–175° C.) which was then treated with sodium azide (33 g) and ammonium chloride (27 g) in dimethylformamide (120 ml) at 100° C. for 4 hours After cooling, dilution with water (600 ml), acidification with concentrated hydrochloric acid and filtration, 6-(5-tetrazolyl)-2'-isopropoxy-flavone (11 g; m.p. 293°–295° C.) was obtained, after crystallization from chloroform/ethanol.

By using the same method, the following compounds were obtained:

6-(5-tetrazolyl)-2'-(2-methyl-propoxy)-flavone;
6-(5-tetrazolyl)-2'-(1-methyl-propoxy)-flavone;
6-(5-tetrazolyl)-2'-propoxy-flavone;
6-(5-tetrazolyl)-2'-butoxy-flavone;
6-(5-tetrazolyl)-2'-(2-ethoxy-ethoxy)-flavone;
7-(5-tetrazolyl)-2'-isopropoxy-flavone;
7-(5-tetrazolyl)-2'-(2-methyl-propoxy)-flavone.

EXAMPLE 17

By proceeding as described in Example 16, starting from 6-carboxamido-2-(3'-pyridyl)-chromone, prepared from the corresponding ethylester with gaseous ammonia in ethanol at 0° C. for 6 hours, 6-(5-tetrazolyl)-2-(3'-pyridyl)-chromone (yield = 85%) was obtained.

By using the same method, the following compounds were obtained:

6-(5-tetrazolyl)-2-(2'-pyridyl)-chromone
6-(5-tetrazolyl)-2-(4'-pyridyl)-chromone
6-(5-tetrazolyl)-2-(2'-furyl)-chromone
6-(5-tetrazolyl)-2-(2'-pyrazinyl)-chromone

EXAMPLE 18

6-carboxy-2'-isopropoxy-flavone (6.3 g) suspended in benzene (25 ml) was treated with thionyl chloride (1.8 ml) at reflux temperature for an hour. The solution was then evaporated to dryness under vacuum, and the residue was dissolved in 1,2-dichloroethane (45 ml) and treated with 5-amino-tetrazole (2 g) and sodium bicarbonate (2.7 g) under stirring at room temperature for 3 hours. The precipitate, so obtained, was filtered, washed with water, and crystallised from dimethyl-formamide to give 6-(5-tetrazolyl-carboxamido)-2'-isopropoxy-flavone (4 g; m.p. 275°–278° C).

By proceeding analogously, the following compounds were prepared:

6-(5-tetrazolyl-carboxamido)-2'-(2-methyl-propoxy)-flavone;
6-(5-tetrazolyl-carboxamido)-2'-(1-methyl-propoxy)-flavone;
6-(5-tetrazolyl-carboxamido)-2'-(2-hydroxy-propoxy)-flavone;
6-(5-tetrazolyl-carboxamido)-2'-(3-hydroxy-propoxy)-flavone;
6-(5-tetrazolyl-carboxamido)-2'-(2-hydroxy-2-methyl-propoxy)-flavone;
6-(5-tetrazolyl-carboxamido)-2'-(2-hydroxy-2-methyl-butoxy)-flavone;
6-(5-tetrazolyl-carboxamido)-2'-(2-hydroxy-3-methyl-butoxy)-flavone.

EXAMPLE 19

6-carboxy-2'-isopropoxy-flavone (3.2 g) was treated with a hot aqueous solution containing sodium bicarbonate (800 mg). The small undissolved portion of acid was filtered off and the clear solution was concentrated under vacuum nearly to dryness. By treatment with acetone (200 ml), crystallisation of the sodium salt of 6-carboxy-2'-isopropoxy-flavone (3.1 g; m.p.>300° C.) was obtained.

By proceeding analogously, the sodium salts of the following compounds were prepared:

6-carboxy-2'-(2-methyl-propoxy)-flavone;
6-carboxy-2'-(1-methyl-propoxy)-flavone;
6-carboxy-2'-(2-hydroxy-propoxy)-flavone;
6-carboxy-2'-(3-hydroxy-propoxy)-flavone;
6-carboxy-2'-(2-hydroxy-2-methyl-propoxy)-flavone;
6-carboxy-2'-(2-hydroxy-2-methyl-butoxy)-flavone;
6-carboxy-2'-(2-hydroxy-3-methyl-butoxy)-flavone.
6-carboxy-2-(2'-pyrazinyl)-chromone.

EXAMPLE 20

The sodium salt of 6-carboxy-2'-isopropoxy-flavone (5 g) prepared according to Example 19, suspended in dimethylformamide (50 ml) was treated with chloromethyl-pivalate (5 ml) and triethylamine (1.5 ml) at 70° C. for 16 hours. The mixture was then cooled, diluted with water (500 ml), extracted with ethylacetate, and the organic phase was washed with sodium bicarbonate 5%, then with water, finally evaporated to dryness. The residue was crystallised with isopropylether to give pivaloxymethyl ester of 6-carboxy-2'-isopropoxy-flavone (3.9 g; m.p. 102°–104° C).

By using the same method, pivaloxymethylesters of the following compounds were obtained:

6-carboxy-2'-(2-methyl-propoxy)-flavone
6-carboxy-2'-(1-methyl-propoxy)-flavone
6-carboxy-2'-(2-hydroxy-propoxy)-flavone
6-carboxy-2'-(3-hydroxy-propoxy)-flavone
6-carboxy-2'-(2-hydroxy-2-methyl-propoxy)-flavone
6-carboxy-2'-(2-hydroxy-2-methyl-butoxy)-flavone
6-carboxy-2'-(2-hydroxy-3-methyl-butoxy)-flavone.
6-carboxy-2'-(2'-pyrazinyl)-chromone.

EXAMPLE 21

The sodium salt of 6-carboxy-2'-isopropoxy-flavone (4 g) prepared according to Example 19, suspended in dimethylformamide (40 ml) was treated with chloroacetamide (1.25 g) and a few drops of triethylamine at 75° C. for 24 hours. After cooling, dilution with water, acidification with acetic acid filtration, 6-glycolamide ester of 6-carboxy-2'-isopropoxy-flavone (4.2 g; m.p. 230°–232° C.) was obtained, which was hydrolysed in acetic acid (30 ml) and hydrochloric acid 23% (20 ml) at 75° C. for an hour. Dilution with water, filtration, and crystallisation from ethanol gave glycolic ester of 6-carboxy-2'-isopropoxy-flavone (3.1 g; m.p. 210°–212° C.). By proceeding analogously, the glycolic esters of the 6-carboxy-flavones specified at the end of Example 20, were obtained.

EXAMPLE 22

2'-Isopropoxy-flavone-6-carbonylchloride (5.6 g) prepared according to Example 18, dissolved in anhydrous benzene (50 ml) was treated with diethylaminoethanol (4.2 ml) and triethylamine (1 ml) at room temperature for 4 hours. The benzene solution was washed with sodium bicarbonate 5% and water, then evaporated to dryness. The residue was dissolved in acetone (100 ml): by addition of the stoichiometric quantity of concentrated hydrochloric acid, precipitation of the hydrochloride of the diethylaminoethyl ester of the 6-carboxy-2'-isopropoxy-flavone was obtained. The compound (5.4 g; m.p. 215°–217° C.) was recovered by filtration and thoroughly washed with acetone. By using the same method, the hydrochlorides of the diethylaminoethyl esters of the 6-carboxy-flavones specified at the end of Example 20, were obtained.

EXAMPLE 23

2'-isopropoxy-flavone-6-carbonyl-chloride (4.3 g) prepared according to Example 18, dissolved in anhydrous benzene (40 ml) was treated with N-hydroxyethyl-morpholine (3.2 g) and pyridine (1 ml) at room temperature for 24 hours. The benzene solution was washed with aqueous citric acid 40% with sodium bicarbonate and water, then evaporated to dryness. The residue, crystallised from acetone, gave morpholinoethyl-ester of 6-carboxy-2'-isopropoxy-flavone (3.6 g; m.p. 133°–135° C.).

By using the same method, the morpholinoethyl esters of the 6-carboxy-flavones specified at the end of Example 20 were obtained.

EXAMPLE 24

Tablets, each weighing 300 mg and containing 100 mg of the active substance were manufactured as follows:

| Composition (for 10,000 tablets) | |
|---|---|
| 6-carboxy-flavone | 1000 g |
| lactose | 1420 g |
| corn starch | 475 g |
| talc powder | 75 g |
| magnesium stearate | 30 g |

6-Carboxy-flavone, lactose and a half of the corn starch were mixed; the mixture was then forced through a sieve of 0.5 mm openings. Corn starch (35 g) was suspended in warm water (350 ml). The resulting paste was used to granulate the powder mixture. The granules were dried, comminuted on a sieve of sieve size 1.4 mm, then the remaining quantity of starch, talc and magnesium stearate were added, carefully mixed, and processed into tablets using punches of 8 mm diameter.

EXAMPLE 25

Tablets, each weighing 300 mg and containing 100 mg of the active substance, were manufactured as follows:

| Composition (for 10,000 tablets): | |
|---|---|
| 6-carboxy-2'-isopropoxy-flavone | 1000 g |

-continued

| Composition (for 10,000 tablets): | |
|---|---|
| lactose | 1420 g |
| corn starch | 475 g |
| talc powder | 75 g |
| magnesium stearate | 30 g |

The tablets were prepared as described in Example 24.

EXAMPLE 26

| Aerosol formulation: | |
|---|---|
| 6-carboxy-3'-chloro-flavone | 2 % |
| ethaanol | 10 % |
| lecithin | 0.2% |
| mixture of propellant 12 and 114 (70 : 30 mixture) | ad 100 % |

Propellant 12 is dichlorodifluoromethane
Propellant 114 is dichlorotetrafluoroethane.

We claim:

1. A compound of the formula:

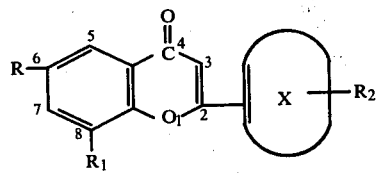

wherein
R is carboxy or —COOR$_3$, wherein R$_3$ is C$_1$–C$_{12}$ alkyl;
R$_1$ is hydrogen, allyl or propyl;
R$_2$ is hydrogen or —(O)$_m$—R$_4$, wherein m is zero or one and R$_4$ is C$_1$–C$_6$ alkyl;
X is pyridyl; and
a pharmaceutically acceptable salt thereof.

2. 6-carboxy-2-(2'-pyridyl)-chromone, as claimed in claim 1.

3. 6-carboxy-2(3'-pyridyl)-chromone, as claimed in claim 1.

4. 6-carboxy-2-(4'-isopropoxy-3'-pyridyl)-chromone, as claimed in claim 1.

5. 6-carboxy-2-[4'-(2-methyl-propoxy)-3'-pyridyl]-chromone, as claimed in claim 1.

6. 6-carboxy-2-[4'-(1-methyl-propoxy)-3'-pyridyl]-chromone, as claimed in claim 1.

7. 6-carboxy-2-[4'-(3-methyl-butoxy)-3'-pyridyl]-chromone, as claimed in claim 1.

8. 6-carboxy-2-(3'-isopropoxy-2'-pyridyl)-chromone, as claimed in claim 1.

9. 6-carboxy-2-[3'-(3-methyl-propoxy)-2'-pyridyl]-chromone, as claimed in claim 1.

10. 6-carboxy-2-[3'-(1-methyl-propoxy)-2'-pyridyl]-chromone, as claimed in claim 1.

11. 6-carboxy-2-[3'-(3-methyl-butoxy)-2'pyridyl]-chromone, as claimed in claim 1.

12. 6-carboxy-2-[3'-(2-hydroxy-propoxy)-2'-pyridyl]-chromone, as claimed in claim 1.

13. 6-carboxy-8-allyl-2-(3'-pyridyl)-chromone, as claimed in claim 1.

14. 6-carboxy-8-propyl-2-(3'-pyridyl)-chromone, as claimed in claim 1.

15. An antiallergic pharmaceutical composition comprising a suitable carrier and/or diluent and, as an active principal, a pharmaceutically effective amount of a compound of the formula

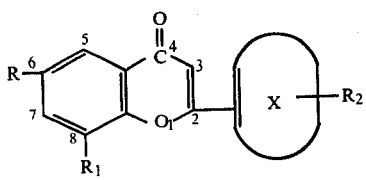

wherein

R is carboxy or —COOR$_3$, wherein R$_3$ is C$_1$–C$_{12}$ alkyl;

R$_1$ is hydrogen, allyl or propyl;

R$_2$ is hydrogen or —(O)—$_m$R$_4$, wherein m is zero or one and R$_4$ is C$_1$–C$_6$ alkyl;

X is pyridyl; and a pharmaceutically acceptable salt thereof.

16. A pharmaceutical composition according to claim 15 in a form suitable for oral administration.

17. A pharmaceutical composition according to claim 15 in a form suitable for parenteral administration.

18. A pharmaceutical composition according to claim 15 in a form suitable for topical administration.

19. A pharmaceutical composition according to claim 15 in a form suitable for inhalation.

20. A method for the prevention and treatment of allergic conditions, said method comprising administering a therapeutically effective amount of a compound of claim 1.

* * * * *